United States Patent [19]
Harman

[11] Patent Number: 4,661,103
[45] Date of Patent: Apr. 28, 1987

[54] MULTIPLE IMPLANT INJECTOR

[75] Inventor: S. Mitchell Harman, Ellicott City, Md.

[73] Assignee: Engineering Development Associates, Ltd., Dayton, Md.

[21] Appl. No.: 835,369

[22] Filed: Mar. 3, 1986

[51] Int. Cl.⁴ ............................................. A61M 5/18
[52] U.S. Cl. ..................................... 604/62; 221/186
[58] Field of Search ................................... 604/60-64, 604/59; 221/186, 187, 198, 232

[56] References Cited

U.S. PATENT DOCUMENTS

| | | | |
|---|---|---|---|
| 1,694,246 | 12/1928 | Boyne | 604/62 |
| 4,154,239 | 5/1979 | Turley | 604/62 |
| 4,451,254 | 5/1984 | Dinius et al. | 604/62 |
| 4,518,324 | 5/1985 | Tarello et al. | 604/62 X |

Primary Examiner—Stephen C. Pellegrino
Attorney, Agent, or Firm—Charles E. Temko

[57] ABSTRACT

An improved magazine type implant injector having a slotted barrel element slidably mounting an integral magazine element and cannula. The barrel element mounts an obturator which projects into the magazine element to serially advance elongated implants to the cannula, each implant advancing a previously engaged implant through the distal end of the cannula for implantation.

5 Claims, 7 Drawing Figures

MULTIPLE IMPLANT INJECTOR

BACKGROUND OF THE INVENTION

This invention relates generally to the field of medical subcutaneous implant injectors of a type suitable for use with human patients, and more particularly to an improved form thereof especially adapted for the implanting of multiple implants at a single site. Reference is made to my co-pending application Ser. No. 703,108 filed Feb. 19, 1985 which discloses and claims a related invention, that application being assigned to the same assignee as the present application. In that disclosure, there is described an injector suitable for use in implanting first and second elongated implants without the necessity of withdrawing the distal end of the cannula from the implant site. That device, while useful, requires reloading of the device after accomplishing the first implant, which operation requires partial disassembly of the component parts. Where the problem of sterility and available working time of the technician are involved, this construction is not as efficacious as would be desired.

SUMMARY OF THE INVENTION

Briefly stated, the invention contemplates the provision of an improved injector of the class described in which provision is made for the serial feeding of multiple implants during a single injection procedure without the necessity of partial disassembly of the injector for reloading. To this end, the device includes the usual components of cannula, a slidably associated barrel having a fixed obturator supported at a proximal end thereof in aligned relation with respect to the cannula, and a hub which supports the proximal end of the cannula and is slidably arranged relative to the inner surface of the barrel. As contrasted with my prior structure, the hub is considerably enlarged and includes a laterally extending magazine which serially feeds successive implants to an integral chamber to be aligned relative to the axis of the cannula. The length of the obturator is substantially shorter than in my prior construction, and is sufficient to move each implant into the proximal end of the cannula, whereby each successive implant transmits motion to the immediately preceding implant to move the same through the cannula and out the distal end thereof. In the preferred embodiment, the construction, with the exception of the cannula is of synthetic resinous materials, and is manufactured at a cost sufficiently low to permit discarding thereof upon the completion of a single implant procedure. Where desired, the device may be provided with a reloadable magazine element to permit use with additional procedures. The slidable disposition of the magazine and chamber as integral elements cooperating with a slidable hub allows for preservation of the principle that the first implant is revealed in situ, as contrasted with being ejected from the end of the cannula, without the necessity of means for rearward displacement of the obturator to allow the subsequent implant to fall from the magazine into the chamber.

BRIEF DESCRIPTION OF THE DRAWINGS

In the drawings, to which reference will be made in the specification, similar reference characters have been employed to designate corresponding parts throughout the several views.

DETAILED DESCRIPTION OF THE DISCLOSED EMBODIMENT

Figure 1:
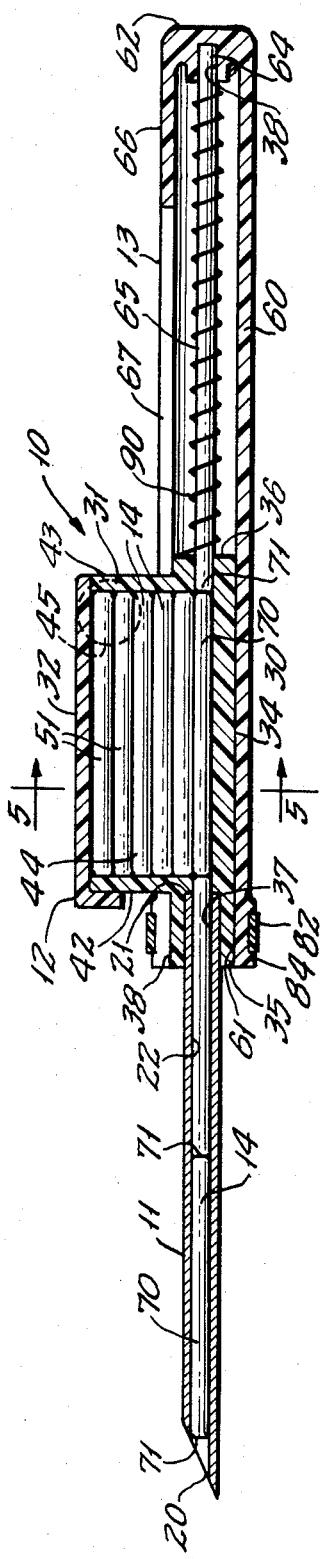
FIG. 1 is a longitudinal central sectional view of an embodiment of the invention.

In accordance with the invention, the device, generally indicated by reference character 10, comprises: an elongated hollow cannula 11, a magazine element 12, a barrel element 13, a plurality of individual implants 14, and a plurality of pushrods 15.

The cannula 11 is of known type, including a sharpened distal end 20 and a relatively blunt proximal end 21, there being a hollow bore 22 communicating therebetween. The cannula will normally be formed of metallic materials and possess a substantial degree of rigidity.

The magazine element 12 is most conveniently formed as a synthetic resinous moulding, and includes an elongated hub member 30 and a magazine shell 31 having a detachable magazine cover 32 on a free end thereof. The hub member 30 is bounded by an outer surface 34 extending between first and second ends 35 and 36, respectively, there being an axially extending bore 37 extending therebetween. A counter-bore portion 38 accommodates the proximal end of the cannula in known manner. Upon engagement with the cannula, the magazine element forms a continuous passage for movement of the implants 14 from the device to the implant site (not shown).

The magazine shell 31 includes side walls 40 and 41 as well as end walls 42 and 43 defining a hollow void or chamber 44.

The cover 32 is also of moulded construction, and includes an outer wall 50 as well as side walls 51 and 52 having laterally extending projections 53 and 54 for engaging corresponding flanges 55 and 56 on the magazine shell. The outer surface of the side walls 51–52 are provided with preferably integrally moulded finger grips 45 and 46 for engagement by the index and third finger of the user.

Figure 5:
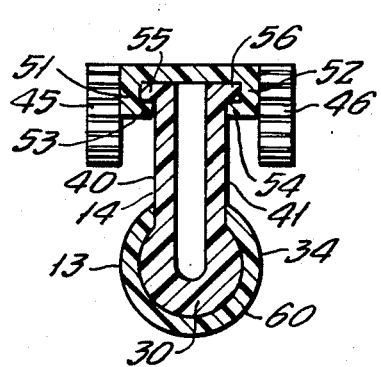
FIG. 5 is a transverse sectional view as seen from the plane 5—5 in FIG. 1.
Figure 7:
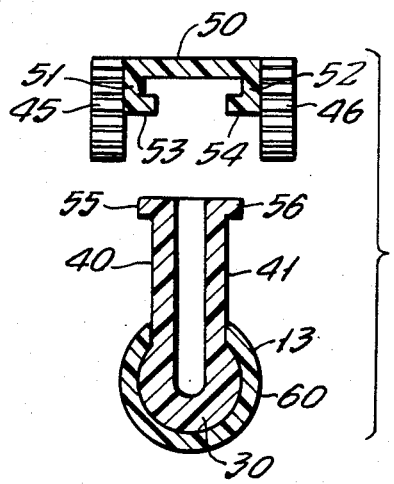
FIG. 7 is an exploded transverse sectional view as seen from the plane 7—7 in FIG. 4.
Figure 6:
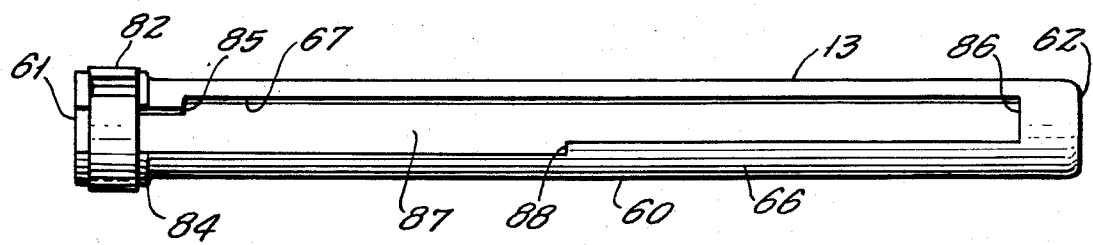
FIG. 6 is a view in elevation of a barrel element forming a part of the embodiment.

FIG. 5 illustrates the communication between the chamber 44 and the bore 37 which forms a loading guide aligned with the cannula.

The barrel element 13 is preferably of moulded construction, and includes an elongated tubular shank 60 having an open end 61 and a closed end 62 the inner surface 63 of which supports the proximal end 64 of an elongated obturator 65. Extending from the outer surface 66 is an elongated slot 67 through which the magazine shell 31 projects.

The implants 14 are of known type, being of elongated cylindrical configuration and bounded by an outer surface 70 and identical first and second ends 71. The push rods 51 are identical in configuration to the implants, but are of inert material to be positioned upon the final implant to serve as means for advancing the final implant to the point of discharge from the distal end of the cannula.

Referring again to the barrel element 13, the magazine is made captive therein for reciprocating movement by the provision of a rotating sleeve 82, which closes the open end of the slot 67. This sleeve rides on a radially extending flange 84. So confined, the magazine shell may move between first and second positions defined by contact of the shell with first and second stop surfaces 85 and 86. Since a portion 87 of the slot is wider than the effective width of the magazine shell 31, a limited amount of rotational movement is possible, enabling the device to be locked against inadvertent relative movement between the above mentioned first and second positions, the locking action being accomplished by contact with a third stop surface 88. Normally the device will be urged to the position shown in FIG. 1 by a small spring 90 which surrounds the obturator.

Figure 2:
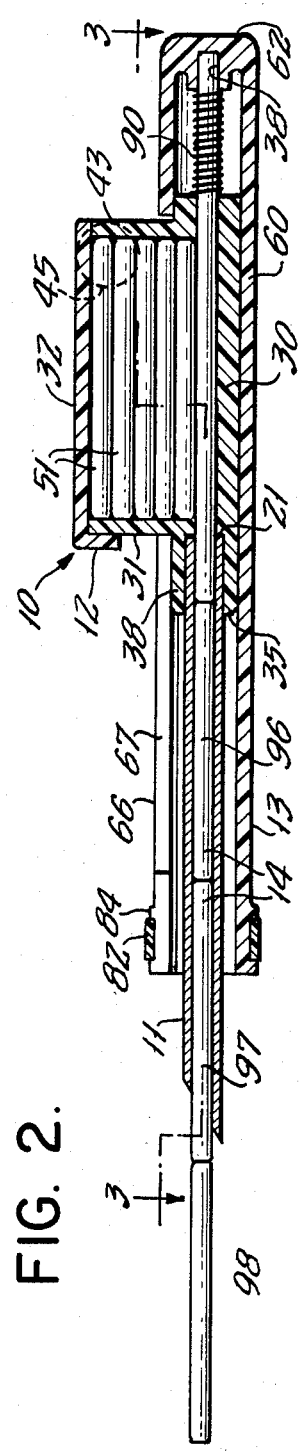
FIG. 2 is a similar longitudinal central sectional view thereof showing certain of the component parts in altered relative position.
Figure 3:
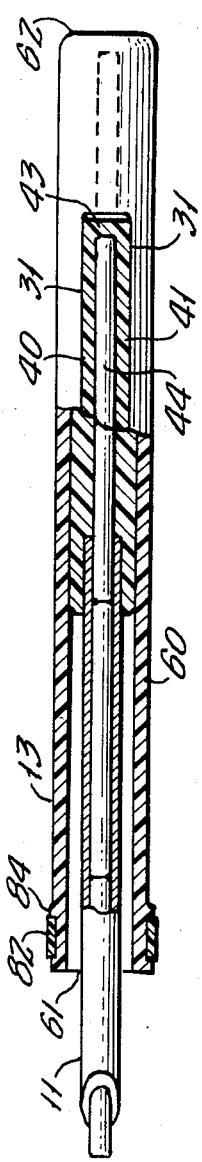
FIG. 3 is a top plan view thereof, partly broken away to show detail.
Figure 4:
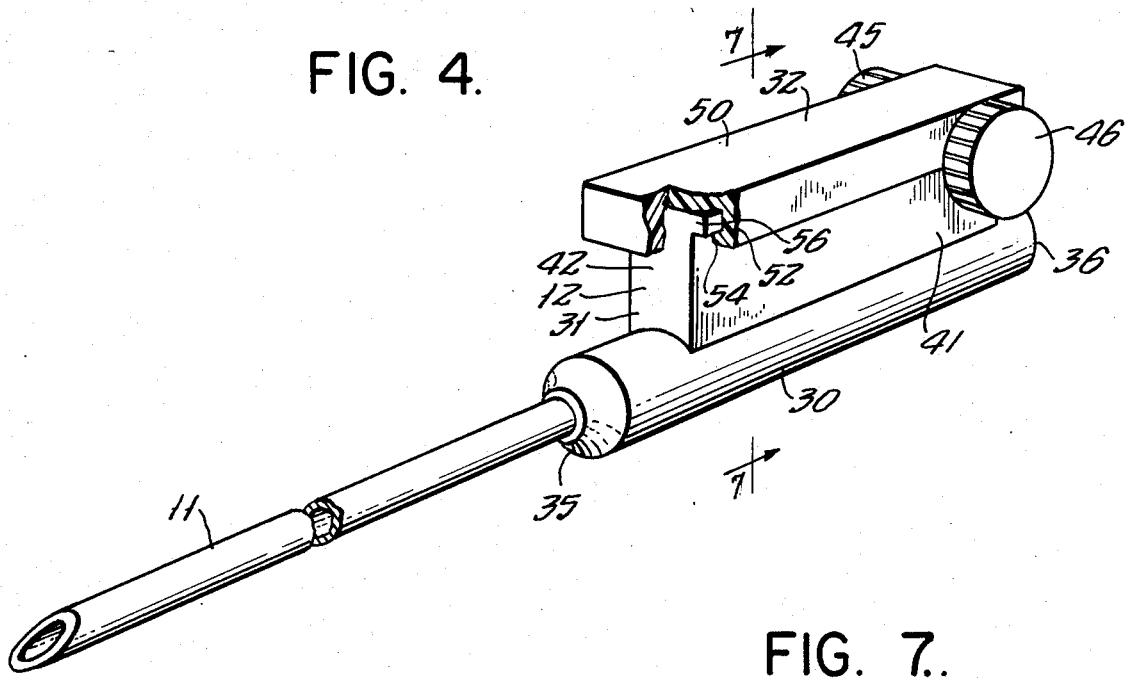
FIG. 4 is a perspective view of a cannula supporting magazine element forming a part of the embodiment.

Operation of the device will be apparent from a consideration of the drawings. Starting with the device in the condition shown in FIG. 1, the distal end of the cannula is positioned subcutaneously with respect to the patient, following which the device is actuated to the position shown in FIG. 2, during which time the obturator will transmit motion to the proximal end of a third implant 96 to a second implant 97 and a first implant 98. It will be appreciated that during this movement, the implant 98 has already been positioned within the patient, and does not move relative to the patient. Rather, the cannula is withdrawn leaving the cannula in situ. Next, while repositioning the angle of the cannula with respect to the patient, without fully withdrawing the cannula, the device is permitted to return to the condition shown in FIG. 1 resulting in withdrawing the obturator from beneath the stack of remaining implants, allowing the fourth implant to drop into the hub and align itself with the implants remaining within the cannula. The operation is again repeated, resulting in the feeding of a second implant adjacent the first implant, and at a slight angle thereto. The process is repeated continuously until all of the implants have been implanted, at which time only the push rods 15 will remain within the cannula, all of the implants having been by this time ejected. Finally, the device is removed from the implant site and discarded.

I wish it to be understood that I do not consider the invention limited to the precise details of structure shown and set forth in this specification, for obvious modifications will occur to those skilled in the art to which the invention pertains.

I claim:

1. An improved multiple medicinal implant injector comprising: a hollow cannula having distal and proximal ends, an elongated implant magazine element having an elongated hollow hub member thereon defining a through bore extending between first and second ends thereof, one of said ends having means thereon engaging said proximal end of said cannula; said magazine element having a hollow laterally extending shell defining a void for retaining elongated implants in stacked relation; an elongated hollow barrel element having a distal end and a closed proximal end, an elongated obturator supported at one end thereof by said closed end of said barrel element, and having an effective length approximating that of an implant; said barrel element having an axially disposed slot therein having first and second transversely extending surfaces, said magazine element being slidably positioned within said barrel element with said shell projecting through said slot for reciprocating movement between first and second positions defined by said transversely extending surfaces; and a plurality of implants positioned in stacked relation within said shell whereby reciprocating movement of said magazine element between said first and second positions serves to move said obturator from beneath stacked implants within said shell to permit successive implants to be aligned with said cannula, subsequent movement of said barrel serving to cause said cannula to move successive implants into the proximal end of said cannula, each successive implant transmitting motion to the immediately proceding implant to result in said implants being moved outwardly of said cannula through the distal end thereof.

2. An injector in accordance with claim 1, further comprising a spring member surrounding said obturator and serving to resiliently urge said magazine element to one of said positions relative to said barrel element, wherein said obturator is withdrawn from beneath said implants in said shell.

3. An injector in accordance with claim 2, further comprising manually engageable grips on outer surfaces of said shell to facilitate one handed operation.

4. An injector in accordance with claim 1, further characterized in said slot in said base element having a third transversely extending surface, said magazine element being rotatable relative to said barrel to prevent unintentional relative axial movement therebetween.

5. An injector in accordance with claim 1, further characterized in said magazine element being integrally moulded from synthetic resinous materials.

* * * * *